United States Patent [19]

Doncheck et al.

[11] Patent Number: 5,204,245
[45] Date of Patent: Apr. 20, 1993

[54] EXTRACTION OF THYMIDINE AND OTHER NUCLEOSIDES

[75] Inventors: James A. Doncheck, Manitowoc; James R. Millis, Kohler, both of Wis.; Paul E. Swanson, Midland, Mich.

[73] Assignee: E. I. du Pont de Nemours and Company, Wilmington, Del.

[21] Appl. No.: 700,659

[22] Filed: May 15, 1991

[51] Int. Cl.$^5$ .................... C12P 19/38; C12P 19/40; C12P 19/30
[52] U.S. Cl. ........................ 435/87; 435/88; 435/89
[58] Field of Search ................ 435/87, 88, 89

[56] References Cited

U.S. PATENT DOCUMENTS

| | | | |
|---|---|---|---|
| 2,130,061 | 9/1938 | Bredereck | 435/87 |
| 3,111,459 | 11/1963 | Motozaki et al. | 435/88 |
| 3,269,917 | 8/1966 | Imada et al. | 435/88 |
| 3,301,767 | 1/1967 | Laufer et al. | 435/89 |
| 3,575,809 | 4/1971 | Shiro et al. | 435/88 |
| 3,668,071 | 6/1972 | Nara et al. | 435/88 |
| 4,452,889 | 6/1984 | Sonoi et al. | 435/88 |
| 4,578,336 | 3/1986 | Sumino et al. | 435/88 |
| 4,593,000 | 6/1986 | Sumino et al. | 435/88 |

FOREIGN PATENT DOCUMENTS 2100731 1/1983 United Kingdom ................ 435/88

*Primary Examiner*—Herbert J. Lilling

[57] ABSTRACT

An enzymatic process for extracting a nucleoside, such as thymidine, from a biomass without substantial thymine production.

8 Claims, 1 Drawing Sheet

EXTRACTION OF THYMIDINE AND OTHER NUCLEOSIDES

FIELD OF THE INVENTION

The present invention relates to enzymatic extraction of nucleosides, such as thymidine, from a biomass.

BACKGROUND OF THE INVENTION

Thymidine is the key component of azidothymidine, which is believed to be an effective treatment of Acquired Immune Deficiency Syndrome (AIDS). Thymidine is obtained currently by synthetic technology. However, the cost of extraction is typically greater than the value of the synthetic thymidine obtained. Particularly, the synthetic technology which is utilized to obtain thymidine requires an expensive multiple step reaction process that yields relatively low quantities of thymidine.

It is an object of the present invention to overcome the inefficiencies of synthetic nucleoside production and provide an abundant and cost-effective source of thymidine.

SUMMARY OF THE INVENTION

The present invention relates to the enzymatic extraction of nucleosides from a biomass. In conducting the extraction process of the present invention, a biomass is treated and then incubated for a time and at a temperature which is sufficient to cause indigenous enzymes to provide one or more nucleosides. The biomass is treated by being ground and introduced into a medium (e.g., an aqueous medium) which contains a dissolved activator that stimulates the indigenous enzymes to extract or provide one or more nucleosides. The incubation process results in a crude liquor which contains a dilute, yet stable, solution of a nucleoside. The nucleoside may be removed or separated from the crude liquor by at least one of the following operations: removal of insolubles, solvent extraction, ionization, chromatographic separation, evaporation and crystallization.

In a key aspect of the present invention, thymidine is enzymatically extracted from barley malt sprouts. In this aspect of the invention, enzymes which are indigenous to the barley malt sprouts may be incubated to extract high yields of thymidine without significant formation of thymine, which is a degradation by-product of thymidine and is not desirable. The concentration of the extracted thymidine may be increased by recycling the product of the enzymatic extraction into a subsequent extraction process. Moreover, certain hydrolytic enzymes which can hydrolyze impurities from the extraction process may be used as processing aids to enhance the effectiveness of the thymidine recovery.

Although the present invention is described in terms of production of the nucleoside thymidine, other useful nucleosides, such as, cytidine, deoxy-guanosine, guanosine, uridine, etc., may be extracted and recovered individually and/or simultaneously with thymidine.

Other advantages and capabilities of the process of the invention will be apparent from the following description.

DETAILED DESCRIPTION OF THE PRESENT INVENTION

Figure 1:
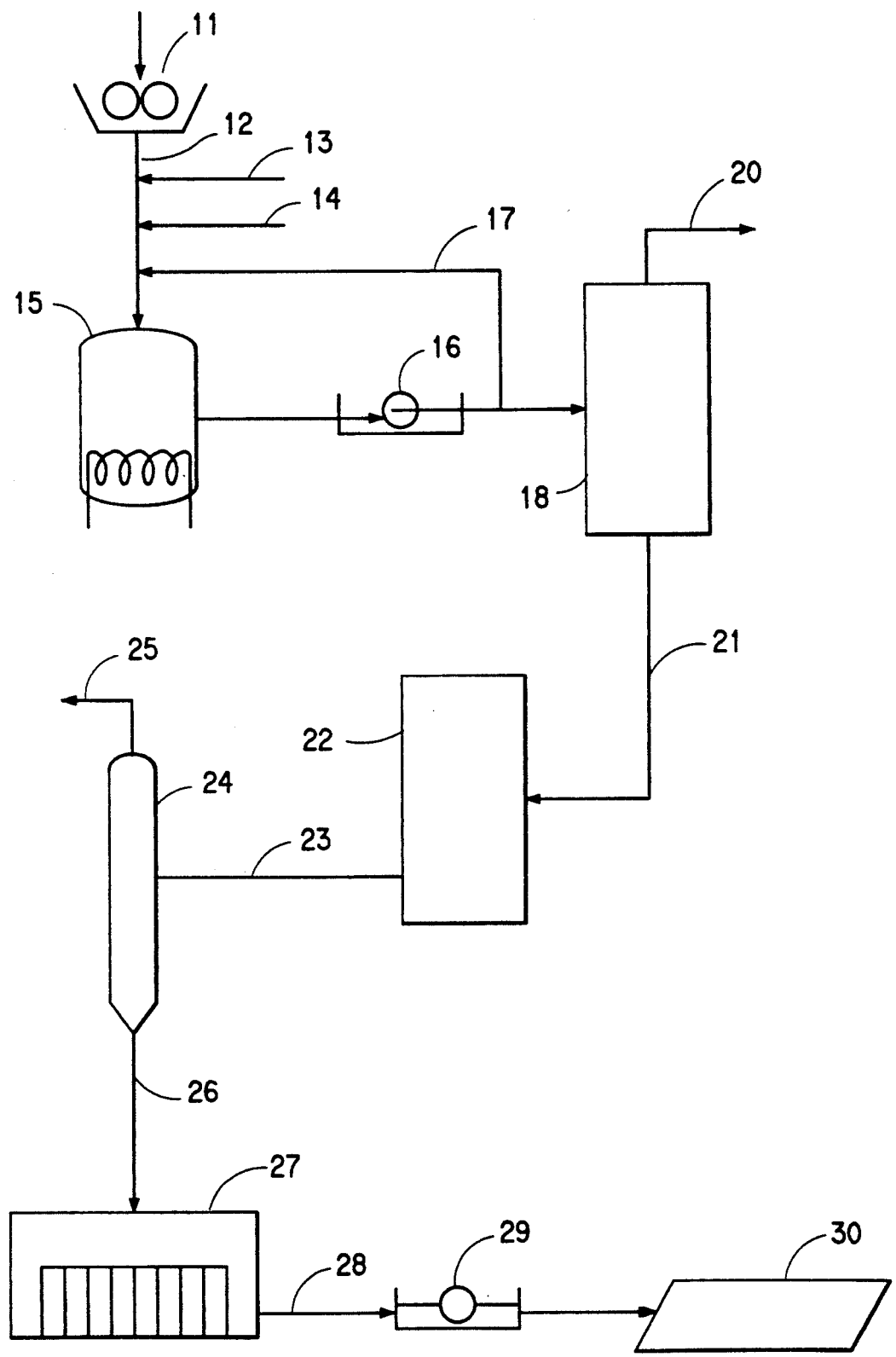
FIG. 1—is a schematic block diagram of the process of the invention.

In practicing the present invention, nucleosides are extracted enzymatically from a biomass. Nucleosides which may be extracted by practicing the invention comprise at least one member of the following group: adenosine, cytidine, deoxy-guanosine, guanosine, thymidine, uridine, etc. A biomass of the type which can be used for practicing the invention comprises at least one member of the following group: barley malt hulls and sprouts, bean sprouts, alfalfa sprouts, brewer's yeast, sigma-Torula yeast, Lake States-Torula yeast, sigma-E. coli, sigma-yeast autolysate, Pseudomonas syringae, etc. The biomass is comminuted or ground to obtain a particulate biomass, preferably ranging from about 100 through about 200 mesh (U.S. standard mesh size). Although a particulate biomass mesh size ranging from about 100 through about 200 is preferred for certain aspects of the present invention, a biomass particle size of about 60 mesh may also be used and produce satisfactory results.

The particles of biomass are contacted (e.g., blended, sprayed, etc.) with a suitable medium to form a dispersion. The dispersion may comprise from about 5% through about 14% by weight biomass particles or solids. A suitable medium may be an aqueous medium (e.g., distilled or tap water) which may also include an activator to stimulate indigenous biomass enzymes extract one or more nucleosides. A suitable activator typically comprises a metallic salt (e.g., chlorides and sulfates of magnesium, calcium, and zinc). The quantity of the activator which may be used should be sufficient to stimulate indigenous enzymes within the biomass to extract at least one nucleoside. In some aspects of the invention, it may be desirable to use two or more activators in conjunction. When thymidine is the desired nucleoside, the concentration of the activator ranges from about 1.0 to 10 millimolar for magnesium and calcium, and from about 0.1 to 1.0 millimolar for zinc.

The pH during the process may be maintained or modified by introducing one or more acids, bases and/or buffers to the biomass dispersion. For example, acids such as $H_2SO_4$, HCl, etc., bases such as NaOH, KOH, CaOH, etc., and/or buffers such as glycine sodium citrate, sodium phosphate, etc., may be introduced into the biomass to maintain or modify the pH. Although, in certain aspects of the invention it may be advantageous to maintain the pH of the biomass within the range of from about 5 to 9, the same is not critical for effective operation of the present invention.

In a key embodiment of the invention, a biomass comprising barley malt sprouts and/or barley malt hulls is used as the biomass source to obtain thymidine. Barley malt sprouts are readily available worldwide as an inexpensive by-product of a brewer's malting process which typically contains a relatively high quantity of extractable thymidine. The ability of the process to use an inexpensive biomass comprising barley malt sprouts permits production of thymidine in a more cost-effective manner. According to the invention, thymidine can be enzymatically extracted from barley malt sprouts without substantial thymine production. Particularly, it is believed that barley malt sprouts lack significant enough quantities of the indigenous enzymes which are capable of degrading thymidine into thymine.

Moreover, without wishing to be bound by any theory or explaination, it is believed that the nucleosides of the present invention are extracted from the biomass as a result of enzymatic hydrolysis of deoxyribonucleic acid (DNA) and ribonucleic acid (RNA). The DNA and RNA within the biomass may be present as a biological polymer comprising nucleosides (e.g., phosphorylated nucleosides). The enzyme, nucleases, may be used to convert the DNA and RNA into nucleotides. The nucleotides may be exposed to the enzyme, phosphatases, to cleave phosphate from the nucleotides to form the desired nucleoside (e.g., cytidine, thymidine, uridine, etc.). Further enzymatic action may remove the ribose sugar molecule from the nucleoside to yield nucleic acid bases (e.g., thymine, uracil, cytosine, adenine, guanine, etc). However, removal of the ribose sugar molecule is typically not desirable for production of the nucleoside thymidine because removal of the ribose sugar molecule from thymidine forms thymine which is an undesired degradation by-product. Moreover, the enzymes which hydrolyize the DNA and RNA of the biomass to extract the desired nucleoside are indigenous to the biomass.

In another embodiment of the present invention, a hydrolytic enzyme which is not typically indigenous to the biomass may be introduced into the biomass dispersion, or mixture, as a processing aid. Suitable hydrolytic enzymes may comprise at least one member of the following group: cellulase, qlucanase, hemicellulase, pectinase, 5'-phosphodiesterase, lysozyme, acid phosphates, etc. Although the present invention may be practiced without using a hydrolytic enzyme, hydrolytic enzymes may serve as an effective processing aid by reducing the viscosity of the biomass dispersion (e.g., by promoting hydrolysis of impurities). A reduced viscosity may enhance the ease with which the invention is practiced, thereby increasing the quantity and quality of the nucleoside recovered. The amount of a hydrolytic enzyme which can be introduced to the biomass dispersion can range from about 0.1 to 1.0% by wt. Preferably, the hydrolytic enzyme will range from about 0.02 to 0.1% by wt.

The biomass dispersion (i.e., an aqueous dispersion including an activator and a hydrolytic enzyme) is introduced into a heating means to incubate and thereby to induce enzymatic extraction of one or more nucleosides. An externally heated, heat-resistant and sealable container or kettle is a preferred heating means. However, any heating means is acceptable which allows production of a crude liquor comprising a stable solution of one or more of the desired nucleosides. The temperature of the heating means is increased to incubate the biomass dispersion. An incubation temperature ranging from about 40° C. through about 60° C. is preferred for production of thymidine; however, the particular temperature which is used may be a function of the process conditions (e.g., pressure, time, etc.) and the particular nucleoside desired. In certain aspects of the invention, the dispersion within the heating means may be agitated, i.e., extraction of the nucleosides may be enhanced by a gentle agitation of the biomass dispersion. Gentle agitation tends to prevent settling of insoluble solids during the enzymatic extraction. The dispersion may be stirred mechanically, vibrated, or agitated via any technique which does not adversely affect the incubation of the biomass dispersion. Upon completion of the incubation period a crude liquor which comprises a stable nucleoside is obtained.

It is to be noted that the pressure which is used during incubation to obtain the crude liquor may range from sub- to super-atmospheric. When the desired nucleoside is thymidine, it is preferable that incubation be conducted at atmospheric pressure. While practicing the invention, a fluid pressure or a vacuum may be applied to the biomass to enhance the rate of nucleoside production or the quality of nucleoside produced (e.g., a pressure may be applied to a liquid to transport the same within a conduit between processing apparatus or stations).

After the biomass is incubated for a time sufficient to produce the crude liquor comprising the desired nucleoside, the liquor may be filtered to remove a portion of the impurities (e.g., insoluble constituents, large molecular weight materials, etc.). Suitable filtering means include a centrifuge, filter press, rotary vacuum filter, precipitator, an ultrafiltration unit, etc. In certain aspects of the present invention, the quantity of nucleoside recovered may be increased by washing the removed impurities.

In one aspect of the invention, a portion or more of the filtered liquor may be recycled to the biomass dispersion, for example, prior to incubation. When using dry ground barley malt sprouts as a starting material to produce thymidine, the sprouts tend to absorb water from the aqueous biomass dispersion. The filtered liquor discussed above, may be recycled and admixed with the make-up water to form the starting aqueous barley malt sprout dispersion. Water which is present in the recycled filtered liquor will usually be absorbed when exposed to the dry, milled barley malt sprouts. To the extent that water from the recycled filtered liquor is absorbed, the concentration of the thymidine within the liquid phase of the biomass dispersion can effectively be increased. The filtered liquor may be recycled a plurality of times (e.g., 5 or more) which can increase the concentration of thymidine because the liquor can contain enzymes which enhance the rate, quality and/or quantity of thymidine that is produced during incubation of the biomass dispersion.

According to another aspect of the invention, the liquor (filtered or unfiltered) after incubation may be stored, transported, etc., without immediately segregating; i.e., separating the nucleoside which has been formed. For example, the crude liquor (i.e., unfiltered) may be shipped to another manufacturing facility for nucleoside separation, or the liquor may be used as a raw material in a divergent operation. The process of the invention may be practiced in a batch or continuous manner.

In any event, the filtered liquor may be processed further to purify the liquor. For example, at least a portion of at least one constituent of the liquid phase within the filtered liquor may be removed by a solvent extraction process (e.g., the constituents of the liquid phase may comprise water, nucleoside, sugars, proteins, solvents, etc.). At least a portion of at least one constituent of the liquid phase may be removed from the filtered liquor by exposing the filtered liquor to a substrate that houses or supports a material which is capable of adsorbing, desorbing, etc., the desired constituent to be removed. Any purification process may be employed to remove a constituent of the liquid phase from the filtered liquor which does not adversely affect the nucleoside therein.

According to another aspect of the invention, the pKa of thymidine (e.g., about 9), which is the highest of all nucleosides, may enhance the ability of thymidine to be separated from the filtered liquor by solvent extraction. The pH of the filtered liquor may be adjusted to a value which is less than the pH at which thymidine ionizes but is greater than the pH at which any other nucleosides that are present ionize (i.e., the undesired nucleosides are in an ionized state). Afterwards, the undesired or ionized nucleoside may be separated from thymidine in the filtered liquor by passing the filtered liquor through an appropriate ion exchange material (e.g., an ion exchange resin). Best results are achieved by proper selection of conditions which segregate the nucleosides based upon their respective pKa values.

In a specific key aspect of the invention, the filtered liquor comprising thymidine as the nucleoside may be purified by a solvent extraction process. This aspect of the present invention is particularly advantageous since the extraction product or purified thymidine liquor does not contain thymine which is a decomposition product of thymidine (i.e., the presence of thymine is not desired). The presence of thymine, however may be an indicator to determine whether the thymidine extraction and/or separation processes are operating effectively (e.g., the presence of thymine may dictate altering at least one process condition). In addition to production of the purified thymidine liquor, the solvent extraction process can also provide one or more desirable by-products, i.e., the solvent may contain other nucleosides such as cytidine, deoxy-guanosine, guanosine, uridine, etc.

The nucleosides within the extraction product or purified liquor may be separated from each other and recovered individually, for example, with a liquid chromatographic separator which will fractionate the nucleosides for recovery by any convenient means. In the case of a purified liquor comprising thymidine, a chromatographic separator is particularly preferred to fractionate and recover liquid thymidine; however, any suitable nucleoside separation process is acceptable which provides useful quantities of the desired nucleoside.

The liquid nucleoside (e.g., liquid thymidine) may be transported to a concentrator means, such as, for example, an evaporator, to remove a significant portion of the non-nucleoside constituents of the liquid phase, thereby concentrating the remaining nucleoside. The evaporated liquid may be released and/or recycled into the nucleoside production process at any appropriate location (e.g., the evaporated liquid may be condensed and admixed with the dry barley malt sprouts which form the biomass dispersion).

For certain end-use applications, the nucleoside can be crystallized from the concentrated liquid phase and optionally dried.

Referring now to the drawing, FIG. 1 shows barley malt sprouts being fed to a dry mill 11, where they are ground to finer than 60 mesh, and normally 100 to 200 mesh (U.S. standard series mesh size). The ground sprouts in line 12 are admixed with an aqueous medium containing low levels of an activator (e.g., a metallic salt), and optionally, with recycled filtered liquor from line 17 to form a dispersion or mixture. Hydrolytic enzymes (e.g., pectinase, cellulase, hemicellulase, glucanase, etc.) may be added as processing aids to reduce the viscosity of the dispersion of barley malt sprouts, thereby allowing easier recovery of any thymidine in line 14. The resulting dispersion is heated and held at about 40° to 60° C. within kettle 15. The dispersion within kettle 15 is gently stirred continuously during the incubation period. The product which comprises crude liquor is then filtered in filter 16, and, as discussed above, some of the filtered liquor may be recycled or returned to feed line 12 by recycle line 17. Large molecular weight impurities are removed by filter 16 which can be either an ultrafiltration unit or a precipitator (e.g., to perform selective precipitation). The filtered liquor is sent to a solvent extraction unit or a unit containing an adsorption/desorption material on a suitable support in 18. A by-product of the solvent extraction process is removed from unit 18 by means of line 20. The resultant solvent extraction product from the filtered liquor yields thymidine and normally also contains other nucleosides, including cytidine, uridine, deoxy-guanosine and guanosine. The solvent extraction product on purified liquor is then sent via line 21 to a liquid chromatographic separator 22 to fractionate the nucleosides to obtain liquid thymidine. The liquid thymidine is then sent via line 23 to an evaporator 24 to concentrate the liquid thymidine. Evaporated liquid from the concentrated thymidine is removed from evaporator 24 via line 25. The concentrated thymidine is fed via line 26 to a crystallization unit 27. The crystalline thymidine is fed via line 28 to a dryer 29 and subsequently to packaging.

Certain aspects of the present invention are demonstrated further by the following Examples which are provided to illustrate and not limit the potential range of equivalents.

In the following Examples, with the exception of the barley malt sprouts and water, reagent grade materials were used.

EXAMPLE 1

Barley malt sprouts, supplied by Busch Agricultural Resources, Manitowac, Wis., were ground to about 60–100 mesh in a Fritz dry mill. Two aqueous biomass dispersions each containing about 5% by weight and about 12.5% by weight of solid ground sprouts were prepared by admixing tap water with the ground sprouts until a total volume of about 3 liters was obtained. Magnesium chloride to about 5 mM, calcium chloride to about 5 mM, zinc chloride to about 0.5 mM, pectinase to about 0.1% (v/v), cellulase to about 0.1% (v/v), and hemicellulase to about 0.2% (w/v) were poured into the dispersions. The dispersions were incubated at about 60° C. for about 12 hours in a 4-liter stainless steel pot, which was covered with a lid, with no stirring. The incubated biomass dispersion was filtered by pouring the biomass through a Buchner funnel. The filtrate was collected and mixed with tap water to form a second biomass dispersion which was incubated in the manner discussed above. The filtrate was again incubated and recycled through a total of five succesive thymidine extraction processes. The filtrate from the first and succeeding incubation extractions was analyzed and the results are reported in Table 1 below.

TABLE 1

|  | Thymidine g/liter | |
| --- | --- | --- |
|  | 5% solids | 12.5% solids |
| 1st Extraction | 0.061 | 0.133 |
| 2nd Extraction | 0.114 | 0.271 |
| 3rd Extraction | 0.145 | 0.488 |
| 4th Extraction | 0.174 | — |
| 5th Extraction | 0.200 | — |

The analyses in Table 1 were performed by cooling the filtrate, followed by HPLC (high pressure liquid chromatography). A review of Table 1 illustrates that recycling a filtrate containing thymidine increases the concentration of thymidine in the final extraction product.

EXAMPLE 2

Barley malt sprouts, supplied by Busch Agricultural Resources, Manitowac, Wis., were ground to about 100-200 mesh with a Fitz dry mill. Seven (7) individual aqueous dispersions each containing about 5% by weight of the solid ground sprouts were prepared. Individual samples were buffered, respectively, to a pH of about 4.0, 5.0, 6.0, 7.0, 8.0, 9.0 and 10.0. The buffers were sodium citrate 100 mM at pH=4.0, 5.0 and 6.0; sodium phosphate at pH 7.0 and 8.0; and glycine at pH 9.0 and 10.0. Magnesium and calcium chloride were added to 5.0 mM and zinc chloride to 0.5 mM in all cases. One series of thymidine extraction or incubation runs was conducted substantially in accordance with Example 1 with the addition of cellulase about 0.1% (v/v), hemicellulase about 0.02% (v/v) and pectinase about 0.1% (v/v). Another series of thymidine extraction runs was conducted substantially in accordance with Example 1 without the addition of hydrolytic enzymes. The runs were all performed in a 4-liter stainless steel pot at about 60° C. with no stirring. The w/w% thymidine extracted, respectively, after about 20, 30 50 and 70 hours was determined and is listed below in Table 2 as a function of the pH which was utilized.

TABLE 2

| pH | W/W % Thymidine Extracted | | | |
|---|---|---|---|---|
| | 20 Hrs. | 30 Hrs. | 50 Hrs. | 70 Hrs. |
| 4.0 | 0.05 | 0.060 | 0.06 | 0.06 |
| 5.0 | 0.10 | 0.12 | 0.12 | 0.12 |
| 6.0 | 0.11 | 0.13 | 0.14 | 0.145 |
| 7.0 | 0.11 | 0.12 | 0.12 | 0.12 |
| 8.0 | 0.10 | 0.115 | 0.115 | 0.115 |
| 9.0 | 0.11 | 0.125 | 0.135 | 0.14 |
| 10.0 | 0.04 | 0.045 | 0.055 | 0.06 |
| No Buffer | 0.11 | 0.13 | 0.14 | 0.145 |

Table 3 reports the results which were obtained when no added hydrolytic enzymes were utilized to extract thymidine.

TABLE 3

| pH | W/W % Thymidine Extracted | | | |
|---|---|---|---|---|
| | 20 Hrs. | 30 Hrs. | 50 Hrs. | 70 Hrs. |
| 4.0 | 0.035 | 0.035 | 0.04 | 0.035 |
| 5.0 | 0.10 | 0.105 | 0.11 | 0.14 |
| 6.0 | 0.12 | 0.125 | 0.13 | 0.13 |
| 7.0 | 0.115 | 0.135 | 0.14 | 0.14 |
| 8.0 | 0.105 | 0.105 | 0.105 | 0.10 |
| 9.0 | 0.125 | 0.13 | 0.13 | 0.135 |
| 10.0 | 0.025 | — | 0.03 | 0.04 |
| No Buffer | 0.115 | 0.14 | 0.145 | 0.14 |

A review of Tables 2 and 3 illustrates that it is advantageous to maintain the pH of the extraction process between about 5 to about 9. Although a buffer may be desirable in certain aspects of the invention, a review of Tables 2 and 3 illustrates that acceptable results may be achieved without a buffer.

EXAMPLE 3

Barley malt sprouts, supplied by Busch Agricultural Resources, Manitowoc, Wis., were ground to about 60-200 mesh with a Fitz dry mill. Two aqueous dispersions containing about 12.5% by weight of the solid ground sprouts were prepared. Both of the aqueous dispersions contained magnesium chloride and calcium chloride to about 5.0 mM, zinc chloride to about 0.5 mM, pectinase to about 0.1% (v/v), cellulase to about 0.1% (v/v), and hemicellulase to about 0.02% (w/v). One of the dispersions contained about 0.2% (w/w) phosphodiesterase and the other dispersion did not. The results of the initial thymidine extraction and extraction after 10, 20 and 30 hours are reported in Table 4. The thymidine was obtained substantially in accordance with the extraction process illustrated in Example 1.

TABLE 4

| | W/W % Thymidine | | | |
|---|---|---|---|---|
| | Initial | (10 Hrs.) | (20 Hrs.) | (30 Hrs.) |
| With Phosphodiesterase | 0.035 | 0.105 | 0.11 | 0.11 |
| Without Phosphodiesterase | 0.035 | 0.105 | 0.11 | 0.11 |

A review of Table 4 illustrates that the hydrolytic enzymes, such as phosphodiesterase, are not required to produce useful quantities of thymidine. However, the hydrolytic enzymes may be utilized to enhance thymidine production by reducing the viscosity of the barley malt dispersion without significantly affecting the resultant thymidine. Specifically, hydrolytic enzymes which substantially only hydrolyze impurities present in the incubation extraction process may serve to enhance the handling or recovery of the thymidine.

Although a few exemplary embodiments of the present invention have been described above in detail, those skilled in this art will readily appreciate that the present invention embraces many combinations and variations other than those exemplified.

What is claimed is:

1. An enzymatic process comprising grinding barley malt sprouts to finer than about 60 mesh, suspending the ground sprouts in water to a solids content of 3 to 15 weight percent, adding 1.0 to 10 mM magnesium salt, 1.0 to 10 mM calcium salt, 0.1 to 1 mM zinc salt, to the dispersion, holding the dispersion at 40° to 60° C. for 12 to 70 hours, and recovering at least one of thymidine, cytidine, uridine, guanosine or deoxy-guanosine from the product.

2. The process of claim 1 wherein one or more of cellulase, hemicellulase, pectinase, glucanose or phosphodiesterase is added to the suspension of ground sprouts being held at 40° to 60° C.

3. The process of claim 2 wherein the product is filtered to remove suspended solids and at least part of the filtrate recycled to and used as process water for the dispersion of ground sprouts being heated.

4. The process of claim 3 wherein the filtrate from the filtration step is treated by a liquid chromatographic separation to recover thymidine from the other nucleosides.

5. The process of claim 4 wherein the thymidine containing product from the chromatographic separation step is concentrated by evaporation.

6. The process of claim 5 wherein the thymidine from the evaporation-concentration step is recovered by crystallization.

7. The process of claim 6 wherein the product from the filtration step is separated by solvent extraction.

8. The process of claim 7 wherein the product from the filtration step is separated by absorption/desorption.

* * * * *

UNITED STATES PATENT AND TRADEMARK OFFICE
CERTIFICATE OF CORRECTION

PATENT NO. : 5,204,245
DATED : April 20, 1993
INVENTOR(S) : James A. Doncheck, James R. Millis and Paul E. Swanson It is certified that error appears in the above-identified patent and that said Letters Patent is hereby corrected as shown below:

Column 4, line 24, change "absorb" to --adsorb--.
Column 4, line 29, change "absorbed" to --adsorbed--.
Column 4, line 32, change "absorbed" to --adsorbed--.
Column 8, line 67, change "absorption/desorption" to
 --adsorption/desorption--.

Signed and Sealed this

Fourth Day of January, 1994

Attest:

BRUCE LEHMAN

Attesting Officer

Commissioner of Patents and Trademarks